United States Patent [19]
Falb et al.

[11] Patent Number: 5,168,867
[45] Date of Patent: Dec. 8, 1992

[54] LOCKING DEVICE FOR A METERING DEVICE FOR AN ANESTHETIC VAPORIZER

[75] Inventors: Wolfgang Falb, Krummesse; Karl-Ludwig Gippert; Ulrich Heim, both of Lübeck; Uvo Hölscher, Stockelsdorf; Siegfried Kiske, Krümmesse; Götz Kullik, Lübeck; Ralf-Ernst Löser, Kreuzkamp; Christoph Maurer, Bad Schwartau, all of Fed. Rep. of Germany

[73] Assignee: Drägerwerk Aktiengesellschaft, Lëbeck, Fed. Rep. of Germany

[21] Appl. No.: 833,326

[22] Filed: Feb. 10, 1992

[30] Foreign Application Priority Data

Feb. 20, 1991 [DE] Fed. Rep. of Germany ....... 4105164

[51] Int. Cl.⁵ .......................... B01F 3/04; A61M 16/18
[52] U.S. Cl. .......................... 128/203.14; 128/200.24; 128/202.22; 128/203.25; 261/39.1
[58] Field of Search ....... 128/203.14, 200.24, 128/202.22, 203.12, 203.13, 203.25, 205.24; 222/153; 261/39.1

[56] References Cited

U.S. PATENT DOCUMENTS

| | | | |
|---|---|---|---|
| 3,910,222 | 10/1975 | Metivier | 128/202.22 X |
| 3,940,064 | 2/1976 | Takaoka | 128/203.25 X |
| 4,017,566 | 4/1977 | Seidel | 261/39.1 X |
| 4,129,621 | 12/1978 | Jones | 261/39.1 |
| 4,818,444 | 4/1989 | Hedderick | 261/39.1 X |
| 4,919,125 | 4/1990 | Heaton | 128/203.14 |
| 4,991,576 | 2/1991 | Henkin | 128/203.28 |

Primary Examiner—Edgar S. Burr
Assistant Examiner—Eric P. Raciti
Attorney, Agent, or Firm—McGlew and Tuttle

[57] ABSTRACT

A locking device 5 for a metering device 3 of an anesthetic vaporizer 1 with an unlocking device 6 for actuating the metering device 3 is provided so as to ensure blocking of the unlocking device 6 in operating states that are unsuitable for the operation of the anesthetic vaporizer 1. The locking device 5 is provided having a final control element 20, 24, 29 that covers a regulating distance that depends on a parameter influencing the operating state of the anesthetic vaporizer 1. This regulating distance of the final control element is transmitted to a blocking device 13 which blocks the unlocking device 6 if the values of the parameter are unsuitable for the operation of the anesthetic vaporizer 1.

8 Claims, 2 Drawing Sheets

LOCKING DEVICE FOR A METERING DEVICE FOR AN ANESTHETIC VAPORIZER

FIELD OF THE INVENTION

The present invention pertains to a locking device for a metering device of an anesthetic vaporizer with a releasing device for actuating the metering device.

It is desirable for safety reasons to secure the metering device of an anesthetic vaporizer against accidental operation in the zero position, i.e., in the position in which no anesthetic is being metered.

BACKGROUND OF THE INVENTION

An anesthetic vaporizer in which a handwheel for adjusting the metering device is locked in the zero position is described in DE-Z: Narkosemittel prazise dosieren mit Dräger-Vapor 19.3 und 19.2[Accurate Metering of Anesthetics with Dräger-Vapor 19.3 and 19.2], KG 5327.20/9047842 of Nov. 1, 1990, Drägerwerk AG. To turn the handwheel from the zero position, locking must first be deactivated depressing a pushbutton.

One disadvantage of this locking device is the fact that it offers protection only against inadvertent opening of the metering device, but not against opening in a state unsuitable for the operation of the anesthetic vaporizer. This is of particular significance in the case of the use of low-boiling anesthetics, whose boiling points are even below room temperature. If the anesthetic vaporizer is not cooled sufficiently, the liquid anesthetic will have partially evaporated, and putting the anesthetic vaporizer into operation would lead to highly incorrect metering. An excessively high or excessively low internal pressure, outside the normal operating pressure of the anesthetic vaporizer, would also lead to incorrect metering.

SUMMARY AND OBJECTS OF THE INVENTION

It is a primary object of the present invention to provide a locking device for a metering device of an anesthetic vaporizer with an unlocking device for actuating the metering device, which is blocked in operating states unsuitable for the operating of the anesthetic vaporizer.

This object is attained in that the locking device has a final control element that moves to a position (covers a regulating distance) that depends on a parameter including the operating state of the anesthetic vaporizer, and the regulating distance of the final control element is transmitted to a blocking device which blocks the release at values of the parameter which are unsuitable for the operation of the anesthetic vaporizer.

The parameter may be the internal temperature of the anesthetic vaporizer, and a bimetallic element, which controls the blocking device via its temperature-dependent regulating device, may be used as the final control element. As an alternative, it is possible to use a fluid-filled elastic bellows as the final control element. The fluid may be a gas or a liquid with a high coefficient of thermal expansion or even a liquid anesthetic which occurs as a gas phase or liquid phase within the bellows. When the boiling point is reached, the vapor pressure rises and the bellows expands.

The stroke of the bellows is designed to be such that the blocking device can be reliably locked or unlocked in a temperature range of a few degrees Celsius. The final control element must be in thermal contact with all the parts of the anesthetic vaporizer which are in contact with the liquid anesthetic. The switching temperature, above which unlocking is blocked and below which unlocking is released, is judiciously selected to be a temperature that is a few degrees Celsius below the boiling point of the liquid anesthetic used.

The pressure in the interior space of the anesthetic vaporizer may also be selected as the parameter. In this case, the final control element is a pressure cell communicating with the interior space, or even a cylinder with a piston. The regulating distance is to be designed to be such that unlocking will be blocked at pressures which are outside the normal operating range of the anesthetic vaporizer.

Additional parameters with correspondingly designed sensors and actuators, e.g., the slope angle of the anesthetic vaporizer, the filling level of the liquid anesthetic, or the fresh gas composition, are also conceivable. An electromagnet or an electric motor may also be used as an actuator.

It is also possible to use as the blocking device a pin moved by the final control element, which engages the unlocking device in unsuitable operating states, so that this will be blocked.

The metering device may be locked in the zero position, as a result of which the anesthetic vaporizer is prevented from being put into operation in unsuitable operating states. However, locking may also be performed in the instantaneous setting of the metering device, as a result of which the setting of the metering device is prevented from being changed at an inopportune time.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENTS

Figure 1:
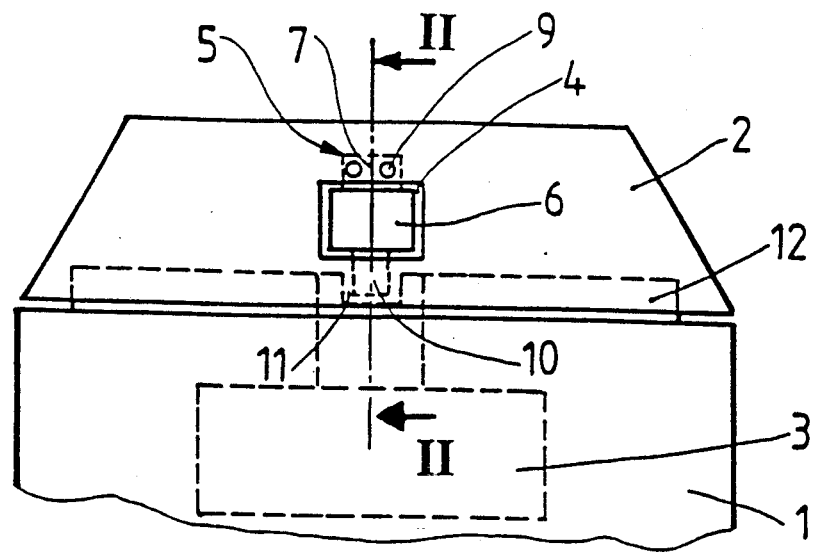
FIG. 1 is a partial view of an anesthetic vaporizer with locking device.

The anesthetic vaporizer 1, shown partially in FIG. 1, is provided with a handwheel 2 for setting the anesthetic concentration by means of a metering device 3 shown schematically.

A locking device 5 is arranged in an opening 4 of said handwheel 2. The locking device include an unlocking device in the form of a pushbutton 6 that is fastened to a leaf spring 7. With its upper end, which projects above said pushbutton 6, said leaf spring 7 is fastened on the inner side 8 of said handwheel 2 by means of two rivets 9. The lower area 10 of said leaf spring 7, which also projects above said pushbutton 6, is tapered. In the zero position of said handwheel 2, in which said metering device 3 is closed, said tapered area 10 extends into a recess 11 of a circumferential housing collar 12 of said anesthetic vaporizer 1 below said handwheel 2. As a result, said handwheel 2 is locked in the zero position. If its setting is to be changed, said tapered area 10 of said leaf spring 7 must be pushed out of said recess 11 by depressing said pushbutton 6.

Figure 2:
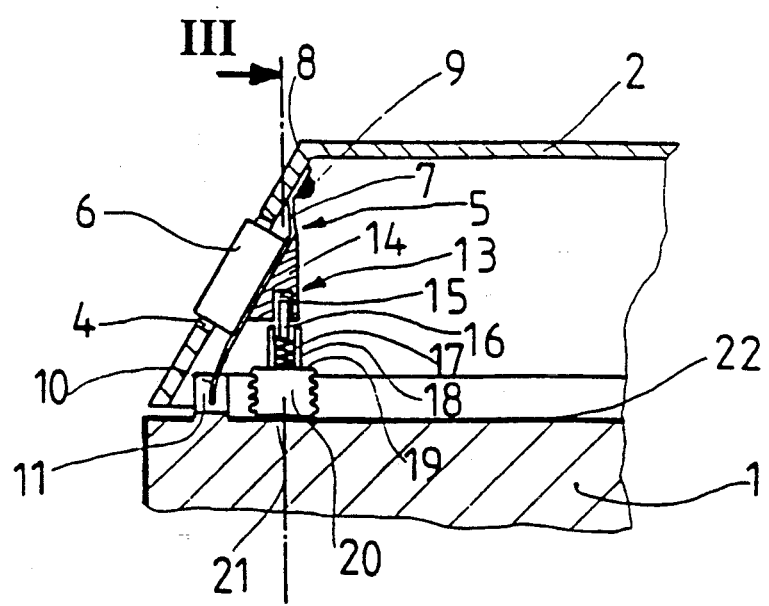
FIG. 2 is a sectional view taken in the direction of line II—II of FIG. 1 through the locking device.

On the inner side of said leaf spring 7 located opposite said pushbutton 6, a blocking device 13 is arranged Section A, FIG. 2. It consists of a block 14, which is fastened to said leaf spring 7 and has a recess 15 into which a pin 16 is able to extend.

Said pin 16 rests on a spring 17 and is guided together with it in a tube 18. Said tube 18 is fastened to the top side 19 of a fluid-filled elastic bellows 20 acting as a final control element. The underside 21 of said bellows 20 is fastened to the top side 22 of said anesthetic vaporizer 1 and is in good thermal contact with the interior spaces of said anesthetic vaporizer 1.

The regulating distance of said bellows 20 is designed so that above a switching temperature (which is a temperature of the interior spaces of the anesthetic vaporizer 1, which is a few degrees Celsius below the boiling point of the liquid anesthetic used), said bellows 20 is extended to the extent that said pin 16 is pressed via said spring 17 into said recess 15 of said block 14.

As a result, said pushbutton 6 is blocked, and it is impossible to unlock the locking device 5 and consequently to put said anesthetic vaporizer 1 into operation. If the temperature of the interior spaces of said anesthetic vaporizer 1 is below the switching temperature, said pin 16 is pulled out of said recess 15, and unlocking is possible.

Figure 3:
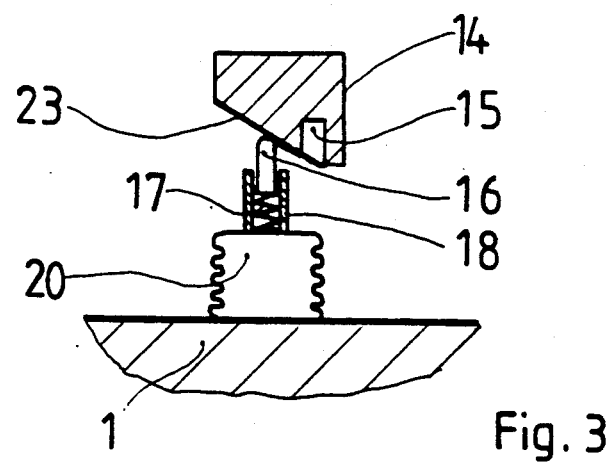
FIG. 3 is sectional view taken in the direction of line III—III of FIG. 2 through the locking device.

If the temperature rises above the switching temperature while said handwheel 2 is in a position outside the zero position, said handwheel 2 still has to be able to be brought to the zero position. The lateral bevel 23 of said block 14, shown in Section B in FIG. 3, is used for this purpose. If said handwheel 2 is moved in the direction of the zero position while said bellows 20 is extended, said bevel 23 of said block 14 pushes said pin 16 into said tube 18 against the force of said spring 17. If said pin 16 is under said recess 15 of said block 14, it jumps into said recess 15, and said pushbutton 6 is blocked.

Figure 4:
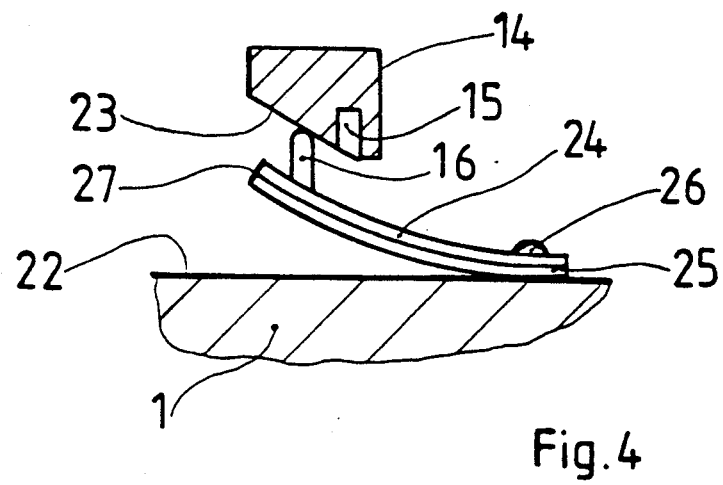
FIG. 4 is a view similar to FIG. 3 providing a sectional view taken in the direction of line III—III of FIG. 2, showing an alternate embodiment of the invention.

FIG. 4 shows an embodiment of the final control element as a bimetallic element 24. One end 25 of said bimetallic element 24 is fastened by a rivet 26 on the top side 22 of said anesthetic vaporizer 1, and a pin 16 is fastened at the other end 27. The function is the same as was described above on the basis of the embodiment with an elastic bellows 20.

Figure 5:
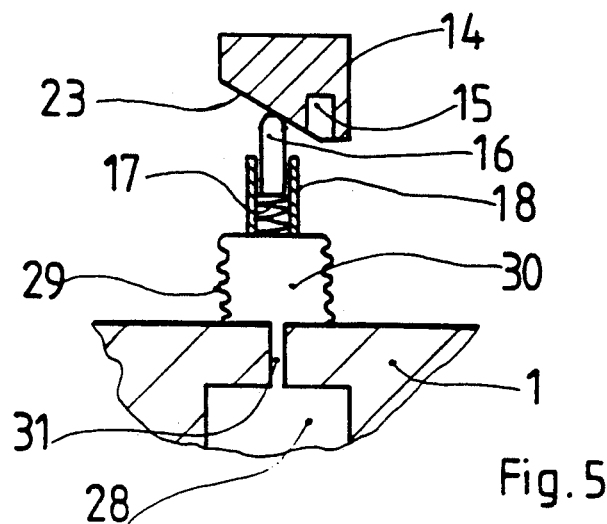
FIG. 5 is a view similar to FIG. 3 providing a sectional view taken in the direction of line III—III of FIG. 2 of an alternate embodiment of the invention.

FIG. 5 shows an embodiment with a pressure cell 29 responding to the pressure in the interior spaces 28 of said anesthetic vaporizer 1. The interior space 30 of said pressure cell 29 is connected via a canal 31 to said interior spaces 28 of said anesthetic vaporizer 1. If the internal pressure is too high, said pressure cell 29 expands to the extent that said pin 16 will block said pushbutton 6, as was described in connection with the design with an elastic bellows 20.

While specific embodiments of the invention have been shown and described in detail to illustrate the application of the principles of the invention, it will be understood that the invention may be embodied otherwise without departing from such principles.

What is claimed is:

1. An apparatus for locking a metering device of a vaporizer for a liquid anesthetic operable depending on a variable operational parameter of the vaporizer comprising:

a metering element for setting the anesthetic dosage connected to the vaporizer;

a locking device operatively engageable with the metering element and having a control element, said control element being movable over a variable regulating distance wherein said regulating distance varies depending on the operational parameter;

unlocking means for disengaging the locking device from the metering element; and blocking means for blocking said unlocking device when the operational parameter is unsuitable for the operation of the anesthetic vaporizer.

2. An apparatus according to claim 1, wherein said parameter is an internal temperature of said anesthetic vaporizer, said control element includes an actuator having a state which is temperature-dependent, said actuator being in thermal connection with an interior space of said anesthetic vaporizer.

3. An apparatus according to claim 2, wherein said control element actuator further comprises means for cooperating with said blocking means for blocking said unlocking device when the internal temperature of said anesthetic vaporizer is below the boiling point of the liquid anesthetic.

4. A locking device according to claim 2, wherein said actuator is provided in the form of a fluid-filled elastic bellows.

5. A locking device according to claim 2, wherein said actuator is provided in the form of a bimetallic element.

6. An apparatus according to claim 1, wherein, said anesthetic vaporizer having an interior space and said parameter is an internal pressure of said interior space, said control element further comprising a pressure cell in fluid communication with said interior space, and said regulating distance depends on the pressure of the interior space.

7. An apparatus according to claim 1, wherein said metering element comprises a block with a recess, and said locking device is formed as a pin engageable with said recess of said block.

8. An apparatus according to claim 1, wherein said anesthetic vaporizer has an inoperative state, and said metering device has a position corresponding to said inoperative state, said locking device is engageable with said metering device at said position corresponding to said inoperative state.

* * * * *

UNITED STATES PATENT AND TRADEMARK OFFICE
CERTIFICATE OF CORRECTION

PATENT NO. : 5,168,867
DATED : December 8, 1992
INVENTOR(S) : Falb et al

It is certified that error appears in the above-identified patent and that said Letters Patent is hereby corrected as shown below:

Title page, item,

[73] Assignee: Drägerwerk Aktiengesellschaft,
Lübeck, Fed. Rep. of Germany

Signed and Sealed this

Nineteenth Day of October, 1993

Attest:

BRUCE LEHMAN

Attesting Officer       Commissioner of Patents and Trademarks